United States Patent [19]

Schaus et al.

[11] Patent Number: 5,466,709
[45] Date of Patent: Nov. 14, 1995

[54] RING-SUBSTITUTED 2-AMINO-1,2,3,4-TETRAHYDRONAPHTHALENES, 3-AMINOCHROMANES, AND 3-AMINOTHIOCHROMANES

[75] Inventors: John M. Schaus, Zionsville; Craig S. Hoechstetter, Indianapolis; Diane Huser, Indianapolis; Charles J. Paget, Indianapolis; Robert D. Titus, Indianapolis, all of Ind.

[73] Assignee: Eli Lilly and Company, Indianapolis, Ind.

[21] Appl. No.: 404,391

[22] Filed: Mar. 14, 1995

Related U.S. Application Data

[62] Division of Ser. No. 168,794, Dec. 16, 1993, Pat. No. 5,426,229, which is a division of Ser. No. 48,553, Apr. 16, 1993, Pat. No. 5,286,753, which is a continuation of Ser. No. 567,985, Aug. 15, 1990, abandoned.

[51] Int. Cl.$^6$ .......................... A61K 31/35; A61K 31/38; C07D 311/04; C07D 335/06
[52] U.S. Cl. .............. 514/432; 514/456; 549/23; 549/404
[58] Field of Search ............... 549/23, 404; 514/432, 514/456

[56] References Cited

U.S. PATENT DOCUMENTS

| | | | |
|---|---|---|---|
| 3,637,740 | 1/1972 | Sarges | 548/578 |
| 3,930,022 | 12/1975 | Hauck et al. | 564/384 |
| 4,410,519 | 10/1983 | Seiler et al. | 514/657 |
| 4,520,030 | 5/1985 | Cavero et al. | 514/629 |
| 4,559,361 | 12/1985 | Oka | 514/619 |
| 4,801,605 | 1/1989 | Hutchison | 514/432 |
| 4,873,262 | 10/1989 | Junge et al. | 514/510 |
| 4,876,284 | 10/1989 | Arvidsson et al. | 564/428 |
| 4,975,461 | 12/1990 | Misra | 514/629 |
| 5,229,410 | 7/1993 | Flaugh et al. | 514/411 |
| 5,306,830 | 4/1994 | Andersson et al. | 549/404 |
| 5,389,687 | 2/1995 | Schaus et al. | 514/657 |

FOREIGN PATENT DOCUMENTS

| | | |
|---|---|---|
| 12347/88 | 9/1988 | Australia . |
| 279150 | 8/1988 | European Pat. Off. . |
| 343830 | 11/1989 | European Pat. Off. . |
| 399983 | 5/1990 | European Pat. Off. . |
| WO81/03491 | 12/1981 | WIPO . |
| WO89/09050 | 10/1989 | WIPO . |
| WO90/12795 | 11/1990 | WIPO . |
| WO90/15047 | 12/1990 | WIPO . |
| WO91/09853 | 7/1991 | WIPO . |

OTHER PUBLICATIONS

Liu et al, *J. Med. Chem.*, vol. 36 (1993) pp. 4221–4229.
Glennon, *J. Med. Chem.*, 30, 1–12 (1987).
Holz, et al., *Psychopharmacology*, 77, 259–267 (1982).
Kline et al., *Chemical Abstracts*, 112, 118413W (1990).
Schohe, et al., *Chemical Abstracts*, 110, 57322A (1989).
Hibert, et al., *Chemical Abstracts*, 115, 279623S (1991).

*Primary Examiner*—Richard L. Raymond
*Attorney, Agent, or Firm*—Joseph A. Jones

[57] ABSTRACT

The present invention provides novel ring-substituted 2-amino-1,2,3,4-tetrahydronaphthalenes, 3-aminochromanes, and 3-aminothiochromanes, including their corresponding sulfoxides and sulfones, which ring-substituted compounds exhibit agonist activity at the serotonin 1A receptor.

2 Claims, No Drawings

RING-SUBSTITUTED 2-AMINO-1,2,3,4-TETRAHYDRONAPHTHALENES, 3-AMINOCHROMANES, AND 3-AMINOTHIOCHROMANES

This application is a division of application Ser. No. 08/168,794 filed on Dec. 16, 1993, now U.S. Pat. No. 5,426,229 which is a division of application Ser. No. 08/048,553, filed Apr. 16, 1993, now U.S. Pat. No. 5,286,753, which was a continuation of application Ser. No. 07/567,985, filed Aug. 15, 1990, now abandoned.

BACKGROUND OF THE INVENTION

Over the last several years it has become apparent that the neurotransmitter serotonin (5-hydroxytryptamine—5-HT) is associated directly or indirectly with a number of physiological phenomena, including appetite, memory, thermoregulation, sleep, sexual behavior, anxiety, depression, and hallucogenic behavior [Glennon, R. A., *J. Med. Chem.* 30, 1 (1987)].

It has been recognized that-there are multiple types of 5-HT receptors. These receptors have been classified as 5-HT$_1$, 5-HT$_2$, and 5-HT$_3$ receptors, with the former being further divided into the sub-classes 5-HT$_{1A}$, 5-HT$_{1B}$, 5-HT$_{1C}$, and 5-HT$_{1D}$.

Selected 2-amino-1,2,3,4-tetrahydronaphthalenes (2-aminotetralins) and 3-aminochromanes have been shown to exhibit binding affinity at the 5-HT$_{1A}$ receptor.

A application Ser. No. 315,750 filed Feb. 27, 1989, refiled and now U.S. Pat. No. 5,389,687, describes certain 2-aminotetralins substituted in the 8-position by formyl, cyano, halo, hydroxymethyl, carboxamido, carboxyl, or alkoxycarbonyl. The compounds are described as exhibiting high binding affinity at the 5-HT$_{1A}$ receptor. 2-aminotetralins in which the 8-position is substituted by, among others, formyl, are also described in EPO patent application No. 272,534. In addition, application Ser. No. 315,752 filed Feb. 27, 1989, refiled and now U.S. Pat. No. 5,389,687, describes other 2-aminotetralins substituted in the 8-position and 3-aminochromanes substituted in the 5-position by sulfides, sulfoxides, and sulfones. These compounds, as well, are described as having binding affinity at the 5-HT$_{1A}$ receptor.

Another class of 2-aminotetralins are described in European Patent Application No. 343,830, published Nov. 29, 1989. These compounds have a piperazinyl or homopiperazinyl moiety in the 2-position and, distinct from the foregoing tetralins, do not exhibit affinity for serotonin receptors but rather inhibit the re-uptake of serotonin. We have now discovered a further class of compounds which, by reason of their 5-HT$_{1A}$ agonist activity, are useful in the treatment, for example, of sexual dysfunction, anxiety, depression, obsessive-compulsive behavior, cognition disorders, emesis, drug abuse, hypertension, excess acid secretion, and eating disorders, such as anorexia.

SUMMARY OF THE INVENTION

The present invention provides novel ring-substituted 2-amino-1,2,3,4-tetrahydronaphthalenes and 3-aminochromanes which are selective agonists at the 5-HT$_{1A}$ receptor.

More specifically, this invention is directed to a compound of the formula

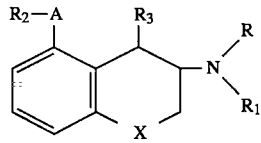

I in which R is C$_1$–C$_4$ alkyl, C$_3$–C$_4$ alkenyl, or cyclopropylmethyl;

R$_3$ is hydrogen; or

R and R$_3$ taken together are a divalent group of the formula —CH$_2$CH$_2$CH$_2$—;

R$_1$ is hydrogen, C$_1$–C$_4$ alkyl, C$_3$–C$_4$ alkenyl, cyclopropylmethyl, aryl(C$_1$–C$_4$-alkyl), —COR$_4$, —(CH$_2$)$_n$S(C$_1$–C$_4$ alkyl) or —(CH$_2$)$_n$CONR$_5$R$_6$;

n is an integer from 1 to 4;

R$_4$ is hydrogen, C$_1$–C$_4$ alkyl, C$_1$–C$_4$ alkoxy, or phenyl;

R$_5$ and R$_6$ are independently hydrogen, a C$_1$–C$_4$ alkyl, or C$_3$–C$_7$ cycloalkyl with the proviso that when one of R$_5$ or R$_6$ is cycloalkyl the other is hydrogen;

X is —CH$_2$—, —O—, —S—,

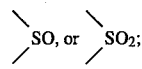

A is

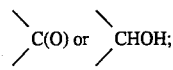

R$_2$ is C$_1$–C$_8$ alkyl, substituted C$_1$–C$_8$ alkyl, C$_2$–C$_4$ alkenyl, aryl, substituted aryl, aryl(C$_1$–C$_4$-alkyl), substituted aryl(C$_1$–C$_4$ alkyl), C$_3$–C$_7$ cycloalkyl-substituted methyl, or C$_3$–C$_7$ cycloalkyl;

and pharmaceutically acceptable acid addition salts thereof.

This invention also provides a pharmaceutical formulation which comprises, in association with a pharmaceutically acceptable carrier, diluent, or excipient, a compound of the formula

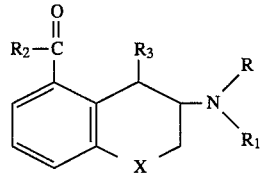

II in which R is C$_1$–C$_4$ alkyl, C$_3$–C$_4$ alkenyl or cyclopropylmethyl;

R$_3$ is hydrogen; or

R and R$_3$ taken together are a divalent group of the formula —CH$_2$CH$_2$CH$_2$—;

R$_1$ is hydrogen, C$_1$–C$_4$ alkyl, C$_3$–C$_4$ alkenyl, cyclopropylmethyl, aryl(C$_1$–C$_4$-alkyl), —COR$_4$, —(CH$_2$)$_n$S(C$_1$–C$_4$ alkyl) or —(CH$_2$)$_n$CONR$_5$R$_6$;

n is an integer from 1 to 4;

R$_4$ is hydrogen, C$_1$–C$_4$ alkyl, C$_1$–C$_4$ alkoxy, or phenyl;

R$_5$ and R$_6$ are independently hydrogen, C$_1$–C$_4$ alkyl, or $C_3-C_7$ cycloalkyl with the proviso that when one of $R_5$ or $R_6$ is cycloalkyl the other is hydrogen;

X is —$CH_2$—, —O—, —S—, >SO, or $SO_2$;

$R_2$ is $C_1-C_8$ alkyl, substituted $C_1-C_8$ alkyl, $C_2-C_4$ alkenyl, aryl, substituted aryl, aryl($C_1-C_4$-alkyl), substituted aryl($C_1-C_4$ alkyl), $C_3-C_7$ cycloalkyl-substituted methyl, or $C_3-C_7$ cycloalkyl;

and pharmaceutically acceptable acid addition salts thereof.

A further embodiment of the invention is a method for effecting a biological response at the 5-HT$_{1A}$ receptor. More particularly, further embodiments are methods for treating a variety of disorders in mammals which may be treated by stimulating 5-HT$_{1A}$ receptors. Included among these disorders are anxiety, depression, sexual dysfunction, obsessive-compulsive behavior, hypertension, excess acid secretion, and eating disorders. Any of these methods employ a compound of the formula

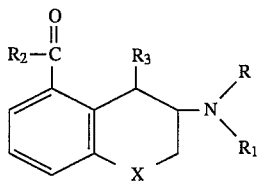

II in which R is $C_1-C_4$ alkyl, $C_3-C_4$ alkenyl or cyclopropylmethyl;

$R_3$ is hydrogen; or

R and $R_3$ taken together are a divalent group of the formula —$CH_2CH_2CH_2$—;

$R_1$ is hydrogen, $C_1-C_4$ alkyl, $C_3-C_4$ alkenyl, cyclopropylmethyl, aryl($C_1-C_4$-alkyl), —$COR_4$, —$(CH_2)_nS(C_1-C_4$ alkyl) or —$(CH_2)_nCONR_5R_6$;

n is an integer from 1 to 4;

$R_4$ is hydrogen, $C_1-C_4$ alkyl, $C_1-C_4$ alkoxy, or phenyl;

$R_5$ and $R_6$ are independently hydrogen, $C_1-C_4$ alkyl, or $C_3-C_7$ cycloalkyl with the proviso that when one of $R_5$ or $R_6$ is cycloalkyl the other is hydrogen;

X is —$CH_2$—, —O—, —S—,

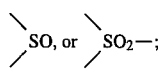

$R_2$ is $C_1-C_8$ alkyl, substituted $C_1-C_8$ alkyl, $C_2-C_4$ alkenyl, aryl, substituted aryl, aryl ($C_1C_4$-alkyl), substituted aryl ($C_1-C_4$ alkyl ), $C_3-C_7$ cycloalkyl-substituted methyl, or $C_1-C_7$ cycloalkyl;

and pharmaceutically acceptable acid addition salts thereof.

DETAILED DESCRIPTION OF THE INVENTION

In the above formulas, the term "$C_1-C_4$ alkyl" means a straight or branched alkyl chain having from one to four carbon atoms. Such $C_1-C_4$ alkyl groups are methyl, ethyl, n-propyl, isopropyl, n-butyl, isobutyl, sec-butyl, and t-butyl.

The term "$C_1-C_8$ alkyl" means a straight or branched alkyl chain having from one to eight carbon atoms. Groups which are included in such term are methyl, ethyl, n-propyl, isopropyl, n-butyl, isobutyl, sec-butyl, t-butyl, n-pentyl, 2-methylbutyl, 3-methylbutyl, n-hexyl, 4-methylpentyl, n-heptyl, 3-ethylpentyl, 2-methylhexyl, 2,3-dimethylpentyl, n-octyl, 3-propylpentyl, 6-methylheptyl, and the like.

The term "$C_1-C_4$ alkoxy" means any of methoxy, ethoxy, n-propoxy, isopropoxy, n-butoxy, isobutoxy, t-butoxy, and sec-butoxy.

The term "aryl" means an aromatic carbocyclic structure. Examples of such ring structures are phenyl, naphthyl, and the like.

The term "$C_3-C_7$ cycloalkyl" means cyclopropyl, cyclobutyl, cyclopentyl, cyclohexyl, and cycloheptyl.

The term "aryl ($C_1-C_4$ alkyl)" means an aromatic carbocyclic structure joined to a $C_1-C_4$ alkyl group. Examples of such groups are benzyl, phenylethyl, α-methylbenzyl, 3-phenylpropyl, α-naphthylmethyl, β-naphthylmethyl, 4-phenylbutyl, and the like.

The term "$C_2-C_4$ alkenyl" means a straight or branched hydrocarbon chain having from two to four carbon atoms and containing one double bond. Groups which are included in such terms are vinyl, 1-methylvinyl, 2-methylvinyl, allyl, 2-butenyl, 3-butenyl, 1-butenyl, 1-methylallyl, 2-methylallyl, and the like.

For purposes herein, the term "$C_3-C_4$ alkenyl" is specifically defined to mean any of allyl, 2-butenyl, 3-butenyl, and 2-methylallyl.

In addition, the $C_1-C_3$alkyl, the aryl, and the aryl ($C_1-C_4$ alkyl) groups may be substituted by one or two moieties. Typical aryl and/or alkyl substituents are $C_1-C_3$ alkoxy, halo, hydroxy, $C_1-C_3$ thioalkyl, and the like. Moreover, the aryl and aryl ($C_1-C_4$ alkyl) groups may also be substituted by a $C_1-C_3$alkyl or a trifluoromethyl group.

In the foregoing, the term "$C_1-C_3$ alkyl" means any of methyl, ethyl, n-propyl, and isopropyl; the term "$C_1-C_3$ alkoxy" means any of methoxy, ethoxy, n-propoxy, and isopropoxy; the term "halo" means any of fluoro, chloro, bromo, and iodo; and the term "$C_1-C_3$thioalkyl" means any of methylthio, ethylthio, n-propylthio, and isopropylthio.

Examples of substituted $C_1-C_3$ alkyl are methoxymethyl, trifluoromethyl, 6-chlorohexyl, 2-bromopropyl, 2-ethoxy-4-iodobutyl, 3-hydroxypentyl, methylthiomethyl, and the like.

Examples of substituted aryl are p-bromophenyl, m-iodophenyl, p-tolyl, o-hydroxyphenyl, β(4-hydroxy)naphthyl, p-(methylthio)phenyl, m-trifluoromethylphenyl, 2-chloro-4-methoxyphenyl, α-(5-chloro)-naphthyl, and the like.

Examples of substituted aryl ($C_1-C_4$ alkyl) are p-chlorobenzyl, p-methoxybenzyl, m-(methylthio)-α-methylbenzyl, 3—(4'-trifluoromethylphenyl)-propyl, o-iodobenzyl, p-methylbenzyl, and the like.

While all of the compounds of the present invention are useful for treating a variety of disorders by virtue of their ability to activate the 5-HT$_{1A}$ receptor in mammals, certain of the compounds are preferred.

Thus, although compounds in which A is

have activity in their own right, their dominant purpose herein is as intermediates to those compounds in which A is

therefore, the latter are preferred.

Moreover, R and $R_1$ preferably are both $C_1-C_4$ alkyl, and, more preferably, both are n-propyl.

X preferably is —$CH_2$—.

$R_2$ preferably is $C_1-C_8$alkyl, and, more preferably, $C_1-C_5$alkyl. Most preferably, $R_2$ is t-butyl.

The compounds of the present invention possess an asymmetric carbon represented by the carbon atom labeled with an asterisk in the following formula:

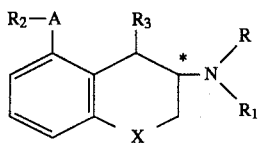

As such, each of the compounds exists as its individual d- and l-stereoisomers and also as the racemic mixture of such isomers. Accordingly, the compounds of the present invention include not only the dl-racemates but also their respective optically active d- and l-isomers.

As mentioned hereinabove, the invention includes pharmaceutically acceptable acid addition salts of the compounds defined by the above formula in which A is

Since the compounds of this invention are amines, they are basic in nature and accordingly react with any of a number of inorganic and organic acids to form pharmaceutically acceptable acid addition salts. Since the free amines of the compounds of this invention are typically oils at room temperature, it is preferable to convert the free amines to their corresponding pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids such as maleic, fumaric, p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid.

In addition, some of these salts may form solvates with water or organic solvents such as ethanol. Such solvates also are included as compounds of this invention.

The following compounds further illustrate compounds contemplated within the scope of this invention:

2-(Di-n-propylamino)-8-acetyl-1,2,3,4-tetrahydronaphthalene;

2-Ethylamino-8-benzoyl-1,2,3,4-tetrahydronaphthalene;

2-(N-Methyl-N-benzylamino)-8-isobutyryl-1,2,3,4tetrahydronaphthalene;

2-Diallylamino-8-phenylacetyl-1,2,3,4-tetrahydronaphthalene;

2-Diethylamino-8-(p-methoxybenzoyl)-1,2,3,4-tetrahydronaphthalene;

2-(Di-n-propylamino)-8-trifluoroacetyl-1,2,3,4-tetrahydronaphthalene;

2-Benzylmethylamino-8-heptanoyl-1,2,3,4-tetrahydronaphthalene;

2-(Di-n-propylamino)-8-(α-methylpropionyl)1,2,3,4-tetrahydronaphthalene;

2-Dimethylamino-8-cyclohexylcarbonyl-1,2,3,4-tetrahydronaphthalene;

2-(Di-cyclopropylmethylamino)-8-(β-chloropentanoyl)-1,2,3,4-tetrahydronaphthalene;

2-(Di-n-propylamino)-8-(p-chlorophenylacetyl)-thio-1,2,3,4-tetrahydronaphthalene;

2-Ethylamino-8-propionyl-1,2,3,4-tetrahydronaphthalene;

2-n-Butylamino-8-(α,α-dimethylpropionyl)-1,2,3,4-tetrahydronaphthalene;

2-(Di-5-propylamino)-8-[β-(4'-methoxyphenyl)propionyl]-1,2,3,4-tetrahydronaphthalene;

2-(Di-n-propylamino)-8-(α,α-dimethylbutyryl)-1,2,3,4-tetrahydronaphthalene;

3-(Di-n-propylamino)-5-acetyl-chromane; and the like.

The compounds of the present invention may be prepared by procedures well known to those of ordinary skill in the art. The compounds in which X is —CH$_2$— and R$_3$ is hydrogen preferably are synthesized by preparation of an 8-bromo-2-tetralone. The 8-bromo-2-tetralone then is reductively aminated with the desired amine to produce the desired 2-amino-8-bromotetralin intermediate. The 8-bromo intermediate then is treated to produce the desired product directly or via the corresponding compound in which the group in the 8-position is R$_2$CH(OH)—.

Schemes for these reactions are as follows:

A. Synthesis of 8-Bromo-2-tetralone

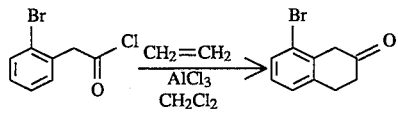

B. Reductive Amination

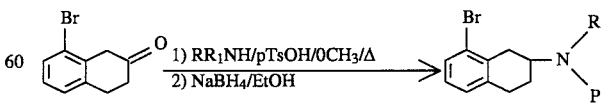

C. Replacement of Bromo Ring Substituent Via Lithiation

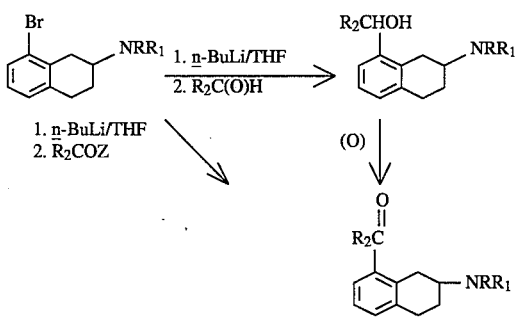

D. Transformation of a Carbonyl Derivative to a Compound of this Invention

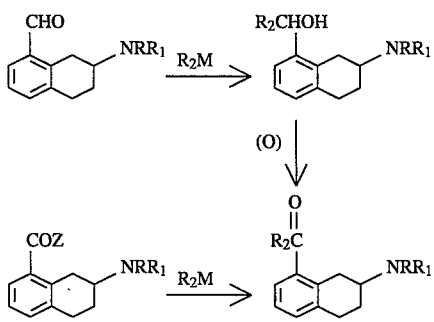

As depicted above, the 8-bromo-2-tetralones represent intermediates which, when reductively aminated and treated, via lithiation, with the appropriate reagent, result in compounds of this invention. When, for example, the reaction involves the use of an aldehyde, the product which results, although having activity in its own right, is, in general, an intermediate of formula I (A is =CHOH) to the preparation of the final product. When the reaction involves the use of an ester, the product is the final product itself (A is =C=O).

The tetralones are available by any of a wide range of recognized methods. For example, they can be produced by a Friedel-Crafts reaction of an appropriately ring-substituted phenylacetyl chloride with ethylene in the presence of aluminum chloride.

The tetralone, once formed, can, by simple reductive amination using the selected amine, be converted to a 2-amino-8-bromo-1,2,3,4-tetrahydronaphthalene useful as an intermediate to a compound of this invention. The tetralone is first reacted with the amine to form the corresponding enamine after which the enamine is reduced with sodium borohydride to the tetrahydronaphthalene.

The 2-amino-8-bromo-1,2,3,4-tetrahydronaphthalene can be used to produce compounds of this invention by formation of a lithium intermediate via a lithiation reaction using an alkyllithium, preferably n-butyllithium. The reactive lithium intermediate then is treated with an appropriate carbonyl compound to produce either the ketone directly or a precursor of the ketone. Hence, treatment of the 8-lithio tetralin with a compound $R_2COZ$, where Z is halo, alkoxy, hydroxy, aryloxy, —S—($C_1$-$C_3$ alkyl),—$OCO_2R'$,

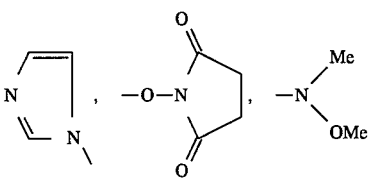

and the like, will, upon workup, yield the desired ketone.

Alternatively, treatment of the 8-lithiotetralin with carbon dioxide and then treatment of the resulting carboxylate with an organolithium reagent, e.g., methyllithium, provides the corresponding ketone. A further alternative synthesis entails reacting the 8-lithiotetralin with an appropriate aldehyde to yield an alcohol of formula I (A=CHOH) which is subsequently oxidized to the ketone. The aforementioned alcohol can also be prepared by addition of a suitable organometallic reagent ($R_2M$ in which M is Li, MgW, ZnW, and the like, W being an appropriate halide) to an 8-formyl-2-aminotetralin. The 8-formyl-2-aminotetralin is prepared by addition of the 8-lithio-2-aminotetralin to dimethylformamide with aqueous workup of the resulting product.

In another approach, the 8-bromo-2-tetralone can first be protected and the bromo substituent converted to the appropriate ketone as described above. The resulting 8-acyl-2-tetralone, after deprotection, can then be reductively aminated to a compound of this invention.

In the foregoing reactions, the 8-lithio tetralin may be replaced by the corresponding Grignard reagent to yield the desired product.

The compounds of this invention in which X is oxygen are available by reductive amination and bromo replacement as in the foregoing, but using 5-bromo-3chromanone. The latter can be produced by a sequence of reactions beginning with m-bromophenol. Briefly, m-bromophenol is treated with allyl bromide in the presence of potassium carbonate to produce allyl 3-bromophenyl ether. The ether is converted to 2-allyl- 3-bromophenol upon heating it in the presence of N,N-dimethylaniline. The phenol, upon reaction with ethyl chloroacetate, is converted to the ethyl ester of 2-allyl-3-(carboxymethoxy)bromobenzene. Upon oxidation using ozone followed by reductive work up, the allyl group is converted to a formylmethyl substituent which is then further oxidized using Jones' Reagent to the carboxymethyl substituent, the resulting product being the ethyl ester of (2-carboxymethyl-3-bromo)phenoxyacetic acid. The partial ester is converted to the diethyl ester using ethanol and gaseous hydrogen chloride. In the presence of potassium t-butoxide, the diester is cyclized to a mixture of 4-ethoxycarbonyl-5-bromo-3-chromanone and 2-ethoxycarbonyl-5-bromo-3chromanone. Upon heating in the presence of acid, the latter is converted to 5-bromo-3-chromanone.

An alternate and improved synthesis of the 5-bromo-3-chromanone involves a sequence of reactions beginning with the ethyl ester of (2-allyl-3-carboxymethoxy)bromobenzene. The bromobenzene is oxidized using ozone to form, upon work-up with dimethyl thioether, the ethyl ester of (2-formylmethyl-3-carboxymethoxy)bromobenzene. The formylmethyl substituent is further oxidized to carboxymethyl using Jones' Reagent, the resulting product being (2-bromo-6-ethoxycarbonylmethoxy)phenylacetic acid. The acid is esterified to the t-butyl ester using t-butyl acetate and sulfuric acid, after which the resulting diester is cyclized in the presence of potassium t-butoxide to 4-t-butoxy-carbonyl-5-bromo-3-chromanone. The t-butoxycarbonyl group then is cleaved using trifluoroacetic acid with formation of the desired 5-bromo-3-chromanone.

The compounds of this invention in which X is sulfur are available by bromo replacement of the corresponding 2-amino-5-bromothiochromanes. The latter are available by a sequence of reactions beginning with m-bromothiophenol. The thiophenol is treated in base with β-chloropropionic acid to produce m-bromophenylthiopropionic acid. The acid then is cyclized with polyphosphoric acid or with thionyl chloride or phosgene and a Lewis acid to produce a mixture of 5-bromo-4-thiochromanone and 7-bromo-4-thiochromanone. The thiochromanone mixture is reduced using, for example, sodium borohydride, to produce 4-bromo-1,2-benzothiapyran which is then oxidized with an organic peroxide to the corresponding sulfoxide having an epoxy group in the 3,4 position. Upon treatment with a Lewis acid, 5-bromo-3-thiochromanone sulfoxide is formed which can be reduced to the corresponding thiochromanone using dimethyl sulfide in the presence of trifluroacetic anhydride, oxalyl chloride, thionyl chloride, and the like, or reductively aminated to the 3-amino-5-bromothiochromane sulfoxide by treatment with the appropriate amine and sodium borohydride. The latter is reduced to the desired 3-amino-5-bromothiochromane using trifluoroacetic anhydride.

Two additional alternative syntheses of the compounds of this invention are via each of two novel intermediates, both of which are part of this invention. The starting material in both sequences, is the previously-described bromo compound in which X, R, $R_1$, and $R_3$ are as herein defined.

In the first sequence the reaction proceeds via a trialkylstannyl intermediate of the formula

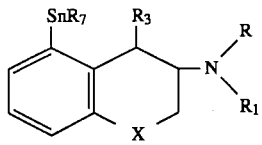   III in which $R_7$ is $C_1$–$C_4$ alkyl.

The foregoing compounds of formula III are prepared by reacting the corresponding bromo compound with n-butyllithium and treating the resulting lithio derivative with chlorotri($C_1$–$C_4$ alkyl)stannane.

The stannyl intermediate then is reacted with an acyl chloride in the presence of a suitable catalyst such as dichlorobis(triphenylphosphine)palladium II or palladium dichloride. This reaction is described in Yamamoto and Yanagi, *Chem. Pharm. Bull.* 30(6), 2003 (1982), Milstein and Stille, *J. Am. Chem. Soc.* 100, 3636 (1978) and *J. Org. Chem.* 44, 1613 (1979).

The second additional sequence proceeds via an alkyne intermediate of the formula

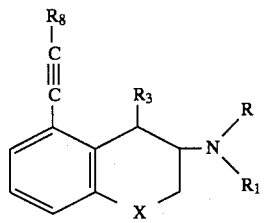   IV in which X, R, $R_1$, and $R_3$ are as above and $R_8$ is hydrogen, $C_1$–$C_7$ alkyl, $C_1$–$C_7$ substituted alkyl, aryl, substituted aryl, aryl($C_1$–$C_3$ alkyl), or substituted aryl ($C_1$–$C_3$ alkyl). The sequence is useful in preparing compounds of this invention in which $R_2$ is $C_1$–$C_8$ alkyl, $C_1$–$C_8$ substituted alkyl, aryl-($C_1$–$C_4$ alkyl), or substituted aryl($C_1$–$C_4$ alkyl).

The foregoing compounds of formula IV are prepared by reacting an iodo compound of the formula

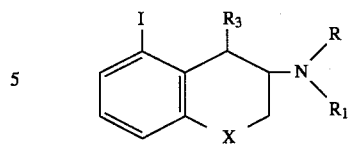

with a 1-alkyne in a suitable inert solvent and in the presence of a palladium catalyst such as tetrakis (triphenylphosphine)palladium or palladium dichloride.

The resulting alkyne is converted to a compound of this invention by hydration in the presence of a suitable catalyst. Suitable catalysts are, for example, protic acids such as HCl, HBr and $H_2SO_4$ as well as mercury (II) salts.

The compounds of this invention also include those in which the groups R and $R_3$ taken together represent a —$CH_2CH_2CH_2$—group. These compounds can be prepared from the corresponding bromo-substituted tetralones, chromanones, or thiochromanones.

The foregoing bromo-substituted compound is reacted with pyrrolidine to form the corresponding 3-pyrrolidino-1,2-dihydronaphthalene, 3-pyrrolidinobenzpyran, or 3-pyrrolidinobenzthiopyran. The 3-pyrrolidino compound then is reacted with acrylamide to produce the corresponding cyclic amide bridging the 3,4-position and comprising the group —NH—CO—$CH_2$—$CH_2$—. The resulting product then is sequentially reduced, first using $HSiEt_3$ and trifluoroacetic acid to reduce the 3,4 double bond and then using $B_2H_6$ or $BH_3.SMe_2$ to reduce the cyclic amide carbonyl. The resulting product is a highly useful intermediate to the compounds of this invention. The intermediate is one in which X is —$CH_2$—, —S—, or —O—, $R_1$ is hydrogen, and R and $R_3$ taken together represent a group of the formula —$CH_2CH_2CH_2$—. Moreover, the intermediate contains a bromo substituent at the 8-position of the tetralin (X=—$CH_2$—) or the 5-position of the chromane (X=O) or thiochromane (X=S).

The foregoing intermediates can be further modified by conversion of the group $R_1$ from hydrogen to $C_1$–$C_4$ alkyl, allyl, cyclopropylmethyl, or aryl($C_1$–$C_4$ alkyl) by reaction with the appropriate organic bromide or iodide.

Further, in those instances in which X is

>SO or >$SO_2$, both are available from the corresponding thiochromanes by oxidation using $NaIO_4$ or a peroxyacid such as peroxyacetic acid, m-chloroperoxybenzoic acid, and the like, in acidic media.

The optically active isomers of the racemates of the invention are also considered part of this invention. Such optically active isomers may be prepared from their respective optically active precursors by the procedures described above, or by resolving the racemic mixtures. This resolution can be carried out in the presence of a resolving agent, by chromatography or by repeated crystallization. Particularly useful resolving agents are d- and l-tartaric acids, d- and l-ditoluoyltartaric acids, and the like.

One particularly useful method for producing optically active isomers of the compounds of this invention is via an 8-substituted-2-tetralone, a 5-substituted-3-chromanone, or a 5-substituted-3-thiochromanone. Any of these intermediates may be reductively alkylated with an optically active α-phenethylamine after which the resulting mixture of diastereomers is separated by recognized methodology, such as chromatography. Cleavage of the α-phenethyl moiety produces a correspondingly substituted, optically active 2-amino-1,2,3,4-tetrahydronaphthalene, 3-aminochromane, or 3-aminothiochromane.

The conditions necessary for removing the phenethyl moiety are relatively severe and can tend to disrupt the integrity of the core tetralin, chromane, or thiochromane molecule. It has been discovered that the cleavage can be carried out in a much more facile and efficient manner requiring only mild cleavage conditions when the particular α-phenethylamine which is used is p-nitro-α-phenethylamine.

Cleavage of the p-nitro-α-phenethyl moiety is achieved by reduction of the p-nitro group followed by acid-catalyzed solvolysis of the resulting p-amino-α-phenethyl moiety. Reduction of the nitro group can be accomplished by a wide range of reducing agents including, for example, titanium trichloride, lithium aluminum hydride, or zinc/acetic acid, or by catalytic hydrogenation. Solvolytic cleavage takes place when the monohydrochloride (or other monobasic salt) of the reduction product is treated with water or an alcohol at room temperature or, in some instances, at elevated temperatures. A particularly convenient condition for removing the p-nitro-α-phenethyl moiety is hydrogenation of the amine monohydrochloride in methanol over a platinum catalyst.

As indicated hereinabove, compounds highly useful as intermediates to the compounds of this invention are the corresponding 8-bromo compounds. It has been discovered that the 8-bromo compounds in their optically active form are not available using routine methodology whereas they can be prepared using the described method employing p-nitro-α-phenethylamine.

The compounds employed as initial starting materials in the synthesis of the compounds of this invention are well known and readily synthesized by standard procedures commonly employed by those of ordinary skill in the art. Moreover, each of the sequences described in the foregoing for producing compounds of this invention involves recognized reactions commonly employed by those of ordinary skill in the art.

The pharmaceutically acceptable acid addition salts of this invention are typically formed by reacting a 1,2,3,4-tetrahydronaphthalene, chromane, thiochromane sulfoxide, or thiochromane sulfone of this invention with an equimolar or excess amount of acid. The reactants are generally combined in a mutual solvent such as diethyl ether or benzene, and the salt normally precipitates out of solution within about one hour to 10 days, and can be isolated by filtration.

The following Examples further illustrate the compounds of the present invention and methods for their synthesis. The Examples are not intended to be limiting to the scope of the invention in any respect and should not be so construed.

EXAMPLE 1

Preparation of 2-Di-n-propylamino-8-pentanoyl-1,2,3,4-tetrahydronaphthalene, oxalate salt.

n-Butyllithium (3.5 mmole, 3.0 ml, 1.2M in hexane) was added to a solution of 8-bromo-2-di-n-propylamino-1,2,3,4-tetrahydronaphthalene (1.0 g, 3.2 mmol) in THF (10 ml) at −78° C. The reaction was stirred at −78° C. for 45 min and then n-pentanal (0.41 ml, 3.9 mmole) was added. After stirring at −78° C. for 5 min, the reaction was warmed to room temperature and poured into dilute HCl solution. The resulting solution was washed once with ether and the ether layer discarded. The aqueous layer was made basic with $NH_4OH$ solution and extracted with methylenechloride. The extract was dried ($Na_2SO_4$) and concentrated to give 0.95 g of the crude product.

Purification by silica gel flash chromatography using 1:1 ether:hexane with a trace of $NH_4OH$ gave 0.68 g of product MS(FD) m/e=317.

Pyridinium chlorochromate (0.9 g, 4.0 mmol) and 4Å molecular sieves (30 g) were added to a solution of 2-di-n-propylamino-8-(1'-hydroxy-1-pentyl)-1,2,3,4-tetrahydronaphthalene (0.63 g=2.0 mmole) in methylene chloride (50 ml). The reaction was stirred at room temperature for 1½ hr at which time the reaction was quenched by the addition of methanol (50 ml). Ether was added until the reaction became cloudy and this material was added to a shorted silica gel column and eluted with ether. The eluent was concentrated. Elution of the column was continued with 10% methanol in methylene chloride and the eluent concentrated to give a residue which was triturated with methanol and filtered through Celite. The filtrate was combined with the crude product from the ether elution and concentrated. Purification of this material on a flash silica gel column using 1:3 ether:hexane with a trace of $NH_4OH$ provided 240 mg of the title compound. MS(FD): m/e=315. The oxalate salt was formed and crystallized from ethylacetate/hexanes to give 165 mg of white crystals. m.p. 107°–108.5° C.

Elemental Analysis: Theory: C, 68.12; H, 8.70; N, 3.45 Found: C, 67.85; H, 8.67; N, 3.41.

EXAMPLE 2

Preparation of 2-Di-n-propylamino-8-trifluoroacetyl-1,2,3,4-tetrahydronaphthalene, hydrobromide salt.

2-Di-n-propylamino-8-bromo-1,2,3,4-tetrahydronaphthalene (1.0 g.; 3.2 mmole) was dissolved in 10 ml. of THF, and the mixture was cooled to −78° C. after which 2.2 ml. of n-butyllithium (1.6M. in hexane) was added. The reaction mixture was stirred at −78° C. for 40 minutes. Ethyl trifluoroacetate (0.42 ml;3.5 mmole) was added and the mixture allowed to warm to room temperature after which it was poured into water, the pH adjusted to 12, and the mixture extracted with methylene chloride. The extract was dried over sodium sulfate and evaporated to give 1.1 g. of a residue.

The residue was purified on a silica gel column which was eluted using a 3:1 mixture of hexane and ether containing a trace of ammonium hydroxide. Fractions containing the impure product were combined to give 240 mg. of a mixture which was further purified by treatment on a silica gel column. The appropriate fractions from this second chromatographic purification were combined with the pure fractions from the first chromatographic purification to obtain 240 mg. of product. The product was converted to the hydrobromide salt and the salt recrystallized from a mixture of ethyl acetate and hexane to give 150 mg. of the title compound as a tan solid, m.p. 142°–144° C.

Elemental Analysis: Theory: C, 52.95; H, 6.17; N, 3.43; Found: C, 53.19; H, 6.08; N, 3.35.

EXAMPLE 3

Preparation of 2-Di-n-propylamino-8-propionyl-1,2,3,4-tetrahydronaphthalene, oxalate salt.

2-Di-n-propylamino-8-bromo-1,2,3,4-tetrahydronaphthalene (8.5 g.; 27.4 mmole) was dissolved in 80 ml. of THF and cooled to −78° C. after which 25.7 ml. of n-butyllithium (1.6M in hexane) were added. The mixture was stirred at −78° C. for one hour after which 2.4 ml. (32.9 mmole) of propionaldehyde were added. The mixture was warmed to room temperature and then poured into water, and extracted with methylene chloride. The extract was dried over sodium sulfate and evaporated to give 9.1 g of a yellow oil.

The oil was placed on a silica gel column and was eluted with a mixture of 3% methanol in methylene chloride containing a trace of ammonium hydroxide. The appropriate fractions were combined to give 6.5 g. (82.0%) of 2-di-n-propylamino-8—(1'-hydroxypropyl)-1,2,3,4-tetrahydronaphthalene as a clear oil.

The foregoing product was dissolved in 250 ml. of methylene chloride, and 17.0 g. (78.7 mmole) of pyridinium chlorochromate (PCC) were added along with 30 g 4A molecular sieves. The mixture was stirred for three hours at room temperature after which 250 ml. of ether and Celite were added. The mixture was poured onto a short silica gel column and eluted with ether. Methanol was added to dissolve the brown sludge which had precipitated upon addition of ether to the reaction. This material was added to the column and eluted with 10% methanol in methylene chloride. The eluent was concentrated to give a brown oil which was further purified by column chromatography employing 2:1 hexanes:ether and then pure ether as solvent. Fractions containing the product were combined and concentrated to give 4.7 g of the product. Tile oxalate salt of 2.5 g of this material was formed and recrystallized three times from ethanol/ether to give the product as a white solid. (1.5 g, m.p. 114.5°–115° C.).

Elemental Analysis: Theory: C, 66.82; H, 8.29; N, 3.71; Found: C, 67.07; H, 8.20; N, 4.00.

EXAMPLE 4

Preparation of 2-Di-n-propylamino-8-butanoyl-1,2,3,4-tetrahydronaphthalene, hydrobromide salt.

2-Di-n-propylamino-8-bromo-1,2,3,4-tetrahydronaphthalene (5.0 g.; 16.1 mmole) was dissolved in 50 ml of THF, and the mixture was cooled to −78° C. after which 1.0 ml of n-butyllithium (0.92M in hexane) were added. The mixture was stirred for 30 minutes, and 1.85 ml, (21.0 mmole) of butyraldehyde were added. The mixture was allowed to warm to room temperature and was stirred overnight after which it was poured into water and extracted with methylene chloride. The extract was dried over sodium sulfate and evaporated to give 6.4 g of a residue. The residue was placed on a silica gel column and was eluted with a mixture of 2% methanol in methylene chloride containing a trace of ammonium hydroxide. The appropriate fractions were combined to give 4.8 g of 2-di-n-propylamino-8-(1'-hydroxybutyl)-1,2,3,4-tetrahydronaphthalene as a thick oil.

The oil (4.0 g.; 13.2 mmole) was dissolved in 200 ml of methylene chloride and 4A molecular sieves (30 g) were added. The mixture was stirred, and 10.0 g (46.2 mmole) PCC were added. Stirring was continued for three hours at room temperature after which the mixture was poured onto a pad of silica gel and eluted sequentially with ether and 3% methanol in methylene chloride containing a trace of ammonium hydroxide to recover the product as a brown oil.

The oil was placed on a silica gel column and was eluted with a mixture of 3% methanol and methylene chloride containing a trace of ammonium hydroxide. The appropriate fractions were combined to obtain an oil which, when dissolved in ether, caused a brown precipitate to form. The precipitate was removed by filtration, and the filtrate was evaporated to give 3.0 g. of a light brown oil as the free base of the title compound.

One gram of the oil was converted to the hydrobromide salt and was recrystallized from a mixture of methanol and ethyl acetate to give 0.9 g of the title compound as tan crystals, m.p. 122°–123° C. Following a second recrystallization, 750 mg were recovered, m.p. 125°–126.5° C.

Elemental Analysis: Theory: C, 62.82; H, 8.43; N, 3.66; Found: C, 63.09; H, 8.22; N, 3.66.

EXAMPLE 5

Preparation of 2-Di-n-propylamino-8-(α-methylpropionyl)-1,2,3,4-tetrahydronaphthalene, hydrobromide salt.

2-Di-n-propylamino-8-bromo-1,2,3,4-tetrahydronaphthalene (1.0 g; 3.2 mmole) was dissolved in 10 ml of THF and cooled to −78° C. after which 3.5 ml (1.0M in hexane) of n-butyllithium were added. To the resulting mixture after 30 minutes was added 0.41 ml (3.5 mmole) of methyl isobutyrate; the mixture was stirred at −10° C. for 30 minutes and then was poured into 10% aqueous hydrochloric acid, washed with ether, and the pH raised to 10. The mixture then was extracted with methylene chloride, and the extract was dried over sodium sulfate and evaporated to give 0.72 g of a residue.

The residue was placed on a silica gel column and was eluted sequentially with a 4:1 mixture of hexane and ether containing a trace of ammonium hydroxide and then a 3:1 mixture of hexane and ether containing a trace of ammonium hydroxide. The appropriate fractions were combined to give 190 mg of the free base of the title compound.

The compound was converted to its hydrobromide salt and was recrystallized from ethyl acetate to give 80 mg of the title compound as tan crystals, m.p. 175°–176.5° C.

Elemental Analysis: Theory: C, 62.82; H, 8.43; N, 3.66; Found: C, 62.54; H, 8.53; N, 3.44.

EXAMPLE 6

Preparation of 2-Di-n-propylamino-8—(β-methylbutyryl)-1,2,3,4-tetrahydronaphthalene, hydrobromide salt.

2-Di-n-propylamino-8-bromo-1,2,3,4-tetrahydronaphthalene (1.0 g; 3.2 mmole) was dissolved in 10 ml of THF and cooled to −78° C. after which 3.5 ml of n-butyllithium (1.0M in hexane) were added. After 30 minutes, 0.53 ml (3.5 mmole) of ethyl isovalerate was added, and the mixture was warmed to −10° C. and maintained for 30 minutes. The mixture then was poured into dilute acid, washed with ether, and the pH adjusted to 10. The mixture was extracted with methylene chloride, and the extract was dried over sodium sulfate and evaporated to give 0.83 g of a residue.

The residue was placed on a silica gel column and was eluted sequentially a 4:1 mixture of hexane and ether containing a trace of ammonium hydroxide and then a 3:1 mixture of hexane and ether containing a trace of ammonium hydroxide. The appropriate fractions were combined to give 50 mg of the free base of the title compound.

The free base was converted to the hydrobromide salt which was recrystallized from a mixture of ethyl acetate and hexane to give 30 mg of the title compound as a tan powder, m.p. 131°–132° C.

Elemental Analysis: Theory: C, 63.63; H, 8.64; N, 3.53; Found: C, 63.35; H, 8.42; N, 3.83.

EXAMPLE 7

Preparation of 2-Di-n-propylamino-8-dimethylpropionyl-1,2,3,4-tetrahydronaphthalene, hydrobromide salt.

2-Di-n-propylamino-8-bromo-1,2,3,4-tetrahydronaphthalene (1.0 g; 3.2 mmole) was dissolved in 20 ml of THF and cooled to −78° C. after which 4.7 ml of n-butyllithium (0.82M in hexane) was added. The mixture was stirred for 30 minutes at −78° C. after which 0.56 ml (4.2 mmole) of methyl trimethyl acetate was added. The mixture was allowed to warm to room temperature and then was poured into water and extracted with methylene chloride. The extract was dried over sodium sulfate and evaporated to give 1.6 g of a residue.

The residue was placed on a silica gel column and was eluted with a 3:1 mixture of hexane and ether containing a trace of ammonium hydroxide. The appropriate fractions were combined to give 140 mg of the free base of the title compound.

The free base was converted to the hydrobromide salt and was recrystallized from methanol/ethyl acetate to give 80 mg of the title compound, m.p. 157°–158° C.

Elemental Analysis: Theory: C, 63.63; H, 8.65; N, 3.53; Found: C, 63.39; H, 8.46; N, 3.43.

EXAMPLE 8

Preparation of 2-Di-n-propylamino-8-cyclohexanecarbonyl-1,2,3,4-tetrahydronaphthalene, oxalate salt.

Method A:

2-Di-n-propylamino-8-bromo-1,2,3,4-tetrahydronaphthalene (1.0 g; 3.2 mmole) was dissolved in 10 ml of THF and cooled to −78° C. after which 2.8 ml of n-butyllithium (1.27M in hexane) were added. The mixture was stirred at −78° C. for 45 minutes after which 0.59 ml (3.5 mmole) of ethyl cyclohexanecarboxylate was added. The mixture was warmed to room temperature and then was poured into a 10% hydrochloric acid solution, washed with ether, the pH adjusted to 10 with ammonium hydroxide, and extracted with methylene chloride. The extract was dried over sodium sulfate and evaporated to give 0.8 g of a residue.

The residue was placed on a silica gel column and was eluted with a 3:1 mixture of hexane and ether containing a trace of ammonium hydroxide. The appropriate fractions were combined to give 0.36 g of the title compound.

Method B:

Butyllithium (1.2M in hexane, 3.0 ml, 3.5 mmole) was added to a solution of 8-bromo-2-di-n-propylamino-1,2,3,4-tetrahydronaphthylene (1.0 g, 3.2 mmole) in THF (10 ml) at −78° and stirred for 45 minutes. Cyclohexanecarboxaldehyde (0.47 ml, 3.9 mmole) was added. The reaction was stirred at −78° for five minutes, warmed to room temperature, poured into dilute HCl solution and washed with ether. The aqueous layer was made basic with NH$_4$OH and extracted with methylene chloride. The extract was dried (Na$_2$SO$_4$) and concentrated to give 1.1 g of the crude product. The crude product was dissolved in methylene chloride (50 ml) and molecular sieves and pyridinium chlorochromate (1.4 g, 6.4 mmole) added. The reaction was stirred at room temperature for two hours. Methanol (50 ml) was added and the reaction concentrated to provide a slurry. The slurry was dissolved in methylene chloride (50 ml) and enough ether was added to give a cloudy solution. This material was added to a pad of silica gel and eluted with ether.

The silica gel pad was eluted with 10% methanol in methylene chloride and the eluent concentrated to give an oily residue. This material was triturated with methanol and filtered through Celite. This filtrate was combined with the ether solution from above and concentrated. This material was dissolved in methylene chloride. Ether was added until the solution became cloudy and then filtered through florisil. The filtrate was concentrated to give 560 mg of an oil which was purified by silica gel flash chromatography using 3:1 hexane:ether containing a trace of NH$_4$OH as solvent. Appropriate fractions were combined and concentrated to give 350 mg of the desired compound. The oxalate salt was formed and crystallized from ethyl acetate/hexane to give 370 mg of a white solid. m.p. 98.5°–100°.

Elemental Analysis: Theory: C, 69.58; H, 8.64; N, 3.25; Found: C, 69.28; H, 8.87; N, 3.00.

EXAMPLE 9

Preparation of 2-Di-n-propylamino-8-benzoyl-1,2,3,4-tetrahydronaphthalene, tosylate salt. 2-Di-n-propylamino-8-bromo-1,2,3,4-tetrahydronaphthalene (1.0 g; 3.2 mmole) was dissolved in 20 ml of THF and cooled to −78° C. after which 3.0 ml of n-butyllithium (1.6M in hexane) was added. The mixture was stirred at −78° C. for one hour after which 0.5 ml (4.8 mmole) of benzaldehyde was added. Stirring was continued for 15 minutes, and the mixture was allowed to warm to room temperature and then was poured into water and extracted with methylene chloride. The extract was dried over sodium sulfate and evaporated to give 1.4 g of a yellow oil.

The oil was placed on a silica gel column and was eluted with a 1:1 mixture of hexane and ether containing a trace of ammonium hydroxide. The appropriate fractions were combined to give 0.9 g of 2-di-n-propyl-amino-8-(α-hydroxybenzyl)-1,2,3,4-tetrahydronaphthalene.

The foregoing product (0.83 g; 2.5 mmole) was dissolved in 50 ml of methylene chloride, and about 1 g of molecular sieves was added followed by 1.9 g (8.6 mmole) of PCC. The mixture was stirred for two hours after which it was diluted with ether and poured onto a silica gel column. The column was eluted with ether and then with a mixture of 10% methanol and methylene chloride. The fractions were combined, and the residue was dissolved in methanol and the solution was filtered through a pad of Celite. The filtrate was evaporated, and the residue was placed on a Florisil column which was eluted with a 2:1 mixture of hexane and ether. The appropriate fractions were combined to give 0.5 g of the free base of the title compound.

The free base was converted to the tosylate salt which was recrystallized from a mixture of acetone and ether to give 125 mg of the title compound as a white powder, m.p. 148.5°–149° C.

Elemental Analysis: Theory: C, 70.97; H, 7.35; N, 2.76; Found: C, 71.18; H, 7.27; N, 2.74.

EXAMPLE 10

Preparation of 2-Di-n-propylamino-8—(a-chlorobenzoyl)-1,2,3,4-tetrahydronaphthalene.

2-Di-n-propylamino-8-bromo-1,2,3,4-tetrahydronaphthalene (1.0 g; 3.2 mmole) was dissolved in 10 ml of THF and cooled to −78° C. after which 3.5 ml of n-butyllithium (1.0M in hexane) were added. The mixture was stirred for one hour at −78° C. after which 680 mg (1.5 equivalents) of 4-chlorobenzaldehyde in THF were added. The mixture was stirred for 15 minutes at −78° C. and then was allowed to warm to room temperature. The mixture was poured into a 10% aqueous hydrochloric acid solution, washed with ether, the pH adjusted to 10 with ammonium hydroxide, and extracted with methylene chloride. The extract was dried over sodium sulfate and evaporated to give 1.5 g of a residue.

The residue was placed on a silica gel column and was eluted with a 1:1 mixture of hexane and ethyl acetate containing a trace of ammonium hydroxide. The appropriate fractions were combined to give 1.3 g of substantially pure 2-di-n-propylamino-8—(α-methyl-4'-chlorobenzyl)-1,2,3,4-tetrahydronaphthalene.

The foregoing product (3.2 mmole) was dissolved in 50 ml of methylene chloride, and 30 g of 4A molecular sieves were added followed by 1.4 g (6.4 mmole) of PCC. The mixture was stirred for one hour and then was diluted with ether and poured through a pad of silica gel and the silica gel rinsed with ether. The filtrate was evaporated. The silica gel was washed with a mixture of 10% methanol and methylene chloride, and the latter filtrate was evaporated and the residue dissolved in methanol and filtered twice. This filtrate was combined with the ether filtrate, and the resultant mixture was placed on a silica gel column and eluted with a 2:1 mixture of hexane and ether containing a trace of ammonium hydroxide. The appropriate fractions were combined to give 0.3 g of the title compound.

ms(FD): m/e=369.

EXAMPLE 11

Preparation of 2-Di-n-propylamino-8-(o-fluorobenzoyl)-1,2,3,4-tetrahydronaphthalene, p-toluenesulfonic acid salt.

2-Di-n-propylamino-8-bromo-1,2,3,4-tetrahydronaphthalene (1.0 g; 3.22 mmole) dissolved in THF (25 ml) was cooled to −78° C., and 2.5 ml of n-butyllithium (1.27M in hexane) were added. After one hour, o-fluorobenzoyl chloride (0.38 ml, 3.22 mmol) was added. The mixture was stirred for 10 minutes at −78° C. after which the reaction was quenched by addition of water at −78° C. The reaction was poured into dilute HCl solution and extracted with methylene chloride. The aqueous layer was made basic with NaOH and extracted with methylene chloride. The basic extract was dried (Na$_2$SO$_4$) and concentrated to give 200 mg of residue which by nmr did not contain product. The extract from the acidic material was dried (Na$_2$SO$_4$) and concentrated to give 2.0 g of a residue. Purification of this material by flash silica gel chromatography using 1:1 ether:hexane containing a trace of ammonium hydroxide as solvent provided the free base of the title compound (340 mg). The salt of 130 mg of this material with p-toluene sulfonic acid was prepared and crystallized from ethyl acetate/ether to provide 118 mg of the title compound. m.p. 107°–109° C.

Elemental Analysis: Theory: C, 68.55; H, 6.90; N, 2.66; Found: C, 68.41; H, 7.02; N, 2.65.

EXAMPLE 12

Preparation of 2-Di-n-propylamino-8—(methoxyacetyl)-1,2,3,4-tetrahydronaphthalene oxalate.

Method A:

2-Di-n-propylamino-8-bromo-1,2,3,4-tetrahydronaphthalene (5.0 g; 16.1 mmole) was dissolved in 25 ml of THF and cooled to −78° C. after which 3.22 ml of n-butyllithium (1M in hexane) was added. The mixture was maintained at −78° C. for 1.5 hours. This solution was transferred via cannula to a solution of methyl methoxyacetate (7.5 ml, 160 mmol) in THF at −78° C. The reaction mixture was stirred at room temperature overnight, poured into NaHCOa solution and extracted with CH$_2$Cl$_2$. The extract was dried (Na$_2$SO$_4$) and concentrated to give 6.8 g of crude product.

The material then was placed on a chromatographic column, and the product was eluted using 4% methanol in methylene chloride containing a trace of ammonium hydroxide. The appropriate fractions were combined to give 1.4 g of the title compound.

The oxalic acid salt was formed and three times recrystallized from ethyl acetate to give the salt as a white powder, m.p. 118° C.

Method B:

a. 2-Di-n-propylamino-8-trimethylstannyl-1,2,3,4-tetrahydronaphthalene.

Butyllithium (1.2M in hexane; 2.8 ml; 3.4 mmol) was added to a solution of 8-bromo-2-di-n-propylamino-1,2,3,4-tetrahydronaphthalene (1 g; 3.22 mmol) in THF (50 ml) at −78° C. After 1.5 hr., a solution of trimethyltin chloride (1.3 g, 2.0 mmol) in THF (20 ml) was added. The reaction mixture was allowed to warm to room temperature, stirred overnight at room temperature, poured into water, and extracted with methylene chloride. The extract was dried (Na$_2$SO$_4$) and concentrated to give the crude product. Purification by chromatography using 1:10 methanol:methylene chloride gave 1.2 g of the desired product which was used directly in the next step.

b. 2-Di-n-propylamino-8-methoxyacetyl-1,2,3,4-tetrahydronaphthalene.

Bis-triphenylphosphine palladium dichloride (120 mg) was added to a solution of 2-dipropylamino-8-trimethylstannyl-1,2,3,4-tetrahydronaphthalene (500 mg, 1.27 mmol) in benzene (20 ml). Methoxyacetyl chloride (1.5 ml; 1.77 g; 16.5 mmol) was added. The reaction mixture was stirred at room temperature overnight and then heated to reflux for 5 hr. The reaction mixture was poured into water and extracted with methylene chloride. The extract was dried (MgSO$_4$) and concentrated to give 800 mg of crude product. Purification by chromatography using 1:10 methanol: methylene chloride as solvent gave 380 mg of 2-di-n-propylamino-8-methoxyacetyl-1,2,3,4-tetrahydronaphthalene.

EXAMPLE 13

Preparation of 2-Di-n-propylamino-8-acetyl-1,2,3,4-tetrahydronaphthalene

Method A:

A solution of n-butyllithium (1.6M in hexane, 15.1 ml, 24.2 mmole) was added to a solution of 8-bromo-2-di-n-propylamino-1,2,3,4-tetrahydronaphthalene (5.0 g, 16.1 mmole) in THF (50 ml) at −78° and the reaction stirred at −78° for one hour. Gaseous carbon dioxide was bubbled through the reaction at −78° until the deep violet color which forms dissipates. Methyllithium (1.4M in ether, 23 ml) was added. The reaction was stirred at −78° for 30 minutes and warmed to room temperature. The reaction was stirred for an additional ten minutes at room temperature at which time the pink color had been lost. An additional 10 ml of the methyllithium solution was added and the reaction became pink once again. After 15 minutes, the pink color was lost and an additional 10 ml of the methyllithium, solution added. The reaction was poured onto ice, made acidic with hydrochloric acid and extracted with ether. The aqueous layer was made basic and extracted with methylenechloride. The basic extracts were dried (Na$_2$SO$_4$) and concentrated to give 3.8 g of crude product. Purification by flash silica gel chromatography using 2:1 hexane:ether containing trace ammonium hydroxide provided the free base of the title compound as a yellow oil (2.7 g, 61%).

The maleate salt was prepared and crystallized from methanol/ethyl acetate/hexane to give the maleate salt. m.p. 115°–116°.

Elemental Analysis: Theory: C, 67.84; H, 8.04; N, 3.60; Found: C, 68.07; H, 8.02; N, 3.55.

Alternatively, the hydrochloride salt can be prepared. Crystallization from ethanol/ether provided the hydrochloride salt as colorless crystals. m.p. 124°–125° C.

Elemental Analysis: Theory: C, 69.77; H, 9.11; N, 4.52; Found: C, 69.91; H, 9.20; N, 4.53.

Method B:

n-Butyllithium (1.6M in hexane, 60.5 ml, 96.8 mmole) was added to a solution of 8-bromo-2-di-n-propylamino-1,2,3,4-tetrahydronaphthalene (20.0 g, 64.5 mmole) in THF (200 ml) at −78° and the reaction stirred at −78° for one hour. Acetaldehyde (4.3 ml, 77.4 mmole) was added and the reaction allowed to warm to room temperature. The reaction was poured into water, made basic with ammonium hydroxide and extracted with methylene chloride. The extract was dried ($Na_2SO_4$) and concentrated to give 21.4 g of a yellow oil.

To a solution of this yellow oil in methylene chloride (800 ml) was added 4Å molecular sieves (30 g) and pyridinium chlorochromate (27.8 g, 129 mmole). The reaction was stirred at room temperature for 1½ hours. Methanol was added and the reaction filtered through a pad of Celite. The filtrate was concentrated and purified by chromatography over Florisil using 2:1 hexane:ether as solvent. The appropriate fractions were combined to give 6.8 g of the desired product. The solids from the filtration through Celite were suspended in 10% Methanol in methylene chloride and purified by Florisil column chromatography using 10% methanol in methylenechloride as solvent. The fractions containing product were combined and concentrated to give a residue which was taken up in a small volume of methylene chloride. Ether was added to this solution until the material became slightly cloudy. The solution was added to a pad of silica gel and eluted with ether. This material was combined with the product from the original filtrate and concentrated to give the methylketone as a light brown oil. (9.9 g).

As noted above, the compounds (Formula I) of this invention, especially those in which A is

>C(O), have binding affinity for the 5-$HT_{1A}$ receptor. Therefore, another embodiment of the present invention is a method of effecting agonist action at the 5-$HT_{1A}$ receptors which comprises administering to a mammal in need thereof a pharmaceutically effective amount of a compound of the invention.

The term "pharmaceutically effective amount", as used herein, represents an amount of a compound of the invention which is capable of binding to serotonin 1A receptors. The specific dose of compound administered according to this invention will, of course, be determined by the particular circumstances surrounding the case, including, for example, the compound administered, the route of administration, and the condition being treated. A typical daily dose generally will contain from about 0.01 mg/kg to about 20 mg/kg of the active compound of this invention. Preferred daily doses generally will be from about 0.05 to about 10 mg/kg, and ideally from about 0.1 to about 5 mg/kg.

The compounds can be administered by a variety of routes including oral, rectal, transdermal, subcutaneous, intravenous, intramuscular, and intranasal. A special feature of the compounds of this invention is that they are extremely selective in effecting agonist action at serotonin 1A receptors relative to other serotonin receptors.

A variety of physiologic functions have been shown to be subject to influence by brain serotonergic neural systems. As such, the compounds of this invention are believed to have the ability to treat in mammals a variety of 5-HT mediated states and disorders such as sexual disorders, eating disorders, depression, alcoholism, pain, senile dementia, anxiety, and smoking. Therefore, the present invention also provides methods of treating the above disorders at rates set forth above for agonist action in mammals at 5-HT receptors.

The following experiment was conducted to demonstrate the ability of the compounds of the present invention to effect agonist action at the serotonin 1A receptors. This general procedure is set forth in Wong et al., *J. Neural Transm.* 71:207–218 (1988).

Male Sprague-Dawley rats (110–150 g) from Harlan Industries (Cumberland, Ind.) were fed a Purina Chow ad libitum for at least 3 days before being used in the studies. Rats were killed by decapitation. The brains were rapidly removed, and the cerebral cortices were dissected out at 4° C.

Brain tissues were homogenized in 0.32M sucrose. After centrifugation at 1000×g for 10 min and then at 17000×g for 20 min, a crude synaptosomal fraction was sedimented. The pellet was suspended in 100 vol of 50 mM Tris-HCl, pH 7.4, incubated at 37° C. for 10 min, and centrifuged at 50000×g for 10 min. The process was repeated and the final pellet was suspended in ice-chilled 50 mM Tris-HCl, pH 7.4. By the radio-ligand binding method, sites specifically labeled by tritiated 8-hydroxy-2-dipropylamino-1,2,3,4-tetrahydronaphthalene ($^3$H-8-OH-DPAT) have been identified as $5$-$HT_{1A}$ receptors.

Binding of ($^3$H-8-OH-DPAT) was performed according to the previously described method [Wong et al., *J. Neural Transm.* 64:251–269 (1985)]. Briefly, synaptosomal membranes isolated from cerebral cortex were incubated at 37° C. for 10 min. in 2 ml of 50 mM Tris-HCl, pH 7.4; 10 μM pargyline; 0.6 mM ascorbic acid; 0.4 nM $^3$H-8-OH-DPAT; and from 1 to 1000 nM of test compound. Binding was terminated by filtering samples under reduced pressure through glass fiber (GFB) filters. The filters were washed twice with 5 ml of ice cold buffer and placed in scintillation vials with 10 ml of PCS (Amersham/Searle) scintillation fluid. Radioactivity was measured with a liquid scintillation spectrometer. Unlabeled 8-OH-DPAT at 10 μM was also included in separate samples to establish non-specific binding. Specific binding of $^3$H-8-OH-DPAT is defined as the difference of radioactivity bound in the absence and in the presence of 10 μM unlabeled 8-OH-DPAT.

The results of the evaluation of various compounds of the present invention are set forth below in Table I. In Table I, the first column provides the Example Number of the compound evaluated; the next 7 columns identify the structure of the compound evaluated when taken with the formula set forth in the heading; the next-succeeding column identifies the salt form of the compound evaluated; and the final column provides the amount of the test compound expressed in nanomolar concentration required to inhibit the binding of $^3$H-8-OH-DPAT) by 50%, and is indicated in Table I as $IC_{50}$.

TABLE I

BINDING AT 5HT$_{1a}$ IN VITRO

| Compound of Example No. | R  | R$_1$ | A  | R$_2$        | R$_3$ | X      | Salt Form     | IC$_{50}$(nM) 5HT$_{1a}$ |
|-------------------------|----|-------|----|--------------|-------|--------|---------------|--------------------------|
| 1                       | Pr | Pr    | CO | n-butyl      | H     | CH$_2$ | oxalate       | 2.2                      |
| 2                       | Pr | Pr    | CO | CF3          | H     | CH$_2$ | hydrobromide  | 29                       |
| 3                       | Pr | Pr    | CO | ethyl        | H     | CH$_2$ | oxalate       | 0.8                      |
| 4                       | Pr | Pr    | CO | n-propyl     | H     | CH$_2$ | hydrobromide  | 3                        |
| 5                       | Pr | Pr    | CO | isopropyl    | H     | CH$_2$ | hydrobromide  | 0.4                      |
| 6                       | Pr | Pr    | CO | isobutyl     | H     | CH$_2$ | hydrobromide  | 0.4                      |
| 7                       | Pr | Pr    | CO | t-butyl      | H     | CH$_2$ | hydrobromide  | 9                        |
| 8                       | Pr | Pr    | CO | cyclohexyl   | H     | CH$_2$ | oxalate       | 0.5                      |
| 9                       | Pr | Pr    | CO | phenyl       | H     | CH$_2$ | tosylate      | 3.7                      |
| 11                      | Pr | Pr    | CO | o-F-phenyl   | B     | CH$_2$ | tosylate      | 0.8                      |
| 12                      | Pr | Pr    | CO | methoxymethyl| H     | CH$_2$ | oxalate       | 5.8                      |
| 13                      | Pr | Pr    | CO | methyl       | H     | CH$_2$ | hydrochloride | 0.8                      |

The compounds of this invention are preferably formulated prior to administration. Therefore, another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methylhydroxybenzoates, propyl hydroxybenzoates, talc, magnesium stearate, and mineral oil. The formulations may additionally include lubricating agents, wetting agents, emulsifying agents, suspending agents, preserving agents, sweetening agents, flavoring agents, and the like. The compositions of the invention may be formulated so as to provide quick, sustained or delayed release of the active ingredient after administration to the patient by employing procedures well known in the art.

The compositions are preferably formulated in a unit dosage form, each dosage generally containing from about 0.1 to about 500 mg, and preferably from about 1 to about 250 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

|                                                                           | Quantity (mg/capsule) |
|---------------------------------------------------------------------------|-----------------------|
| 2-di-n-propylamino-8-acetyl-1,2,3,4-tetrahydronaphthalene hydrochloride   | 250                   |
| starch, dried                                                             | 200                   |
| magnesium stearate                                                        | 10                    |
| Total                                                                     | 460 mg                |

The above ingredients are mixed and filled into hard gelatin capsules in 460 mg quantities.

Formulation 2

A tablet is prepared using the ingredients below:

|                                                                            | Quantity (mg/tablet) |
|----------------------------------------------------------------------------|----------------------|
| 2-di-n-propylamino-8-propionyl-1,2,3,4-tetrahydronaphthalene hydrochloride | 250                  |
| cellulose, microcrystalline                                                | 400                  |
| silicon dioxide, fumed                                                     | 10                   |
| stearic acid                                                               | 5                    |
| Total                                                                      | 665 mg               |

The components are blended and compressed to form tablets each weighing 665 mg.

Formulation 3

An aerosol solution is prepared containing the following components:

|                                                                                       | Weight % |
|---------------------------------------------------------------------------------------|----------|
| 2-diisopropylamino-8-(p-chlorobenzoyl)1,2,3,4-tetrahydronaphthalene dihydrochloride   | 0.25     |
| ethanol                                                                               | 29.75    |

-continued

| | Weight % |
|---|---|
| Propellant 22 | 70.00 |
| (chlorodifluoromethane) | |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | |
|---|---|
| 2-methylethylamino-8-(α,αdimethylpropionyl)-1,2,3,4-tetrahydronaphthalene maleate | 60 mg |
| starch | 45 mg |
| microcrystalline cellulose | 35 mg |
| polyvinylpyrrolidone | 4 mg |
| (as 10% solution in water) | |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| 2-propylamino-8-cyclohexanecarbonyl-1,2,3,4-tetrahydronaphthalene hydrochloride | 80 mg |
| starch | 59 mg |
| microcrystalline cellulose | 59 mg |
| magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| 2-di-n-propylamino-8-methoxy-acetyl-1,2,3,4-tetrahydro-naphthalene hydrochloride | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| 2-diallylamino-8-trifluoroacetyl-1,2,3,4-tetrahydronaphthalene hydrochloride | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| 2-diethylamino-8-phenylacetyl-1,2,3,4-tetrahydronaphthalene hydrochloride | 100 mg |
| isotonic saline | 1000 ml |

The solution of the above ingredients generally is administered intravenously at a rate of 1 ml per minute to a subject suffering from depression.

We claim:

1. A compound of the formula in which R is $C_1$–$C_4$ alkyl, $C_3$–$C_4$ alkenyl, or cyclopropylmethyl;

$R_3$ is hydrogen;

$R_1$ is —$COR_4$ $R_4$ is hydrogen, $C_1$–$C_4$ alkyl, $C_1$–$C_4$ alkoxy, or phenyl;

X is —O—, —S—, >SO, or >$SO_2$;

A is >C(O);

$R_2$ is $C_1$–$C_8$ alkyl, substituted $C_1$–$C_8$ alkyl, $C_2$–$C_4$ alkenyl, aryl, substituted aryl, aryl($C_1$–$C_4$ alkyl), substituted aryl($C_1$–$C_4$ alkyl), $C_3$–$C_7$ cycloalkyl-substituted methyl, or $C_3$–$C_7$ cycloalkyl;

and pharmaceutically acceptable acid addition salts thereof.

2. A pharmaceutical formulation which comprises a compound of claim 1 in association with a pharmaceutically acceptable carrier, diluent, or excipient therefor.

* * * * *